United States Patent
Brown

(10) Patent No.: US 7,550,745 B2
(45) Date of Patent: Jun. 23, 2009

(54) SENSING DEVICE

(75) Inventor: Stephen Charles Brown, Etoy (CH)

(73) Assignee: KBA-GIORI S.A., Lausanne (CH)

( * ) Notice: Subject to any disclaimer, the term of this patent is extended or adjusted under 35 U.S.C. 154(b) by 566 days.

(21) Appl. No.: 10/544,906

(22) PCT Filed: Feb. 4, 2004

(86) PCT No.: PCT/CH2004/000057

§ 371 (c)(1),
(2), (4) Date: Aug. 10, 2005

(87) PCT Pub. No.: WO2004/069541

PCT Pub. Date: Aug. 19, 2004

(65) Prior Publication Data

US 2006/0144266 A1 Jul. 6, 2006

(30) Foreign Application Priority Data

Feb. 10, 2003 (EP) ................................. 03405068

(51) Int. Cl.
*G01N 21/64* (2006.01)
(52) U.S. Cl. .................... 250/461.1; 250/459.1; 283/92
(58) Field of Classification Search ............. 250/458.1, 250/459.1, 461.1, 462.1, 271; 283/92
See application file for complete search history.

(56) References Cited

U.S. PATENT DOCUMENTS

| | | | | |
|---|---|---|---|---|
| 3,105,908 A | * | 10/1963 | Burkhardt et al. | 250/372 |
| 3,522,432 A | * | 8/1970 | Ortlieb | 250/365 |
| 4,451,521 A | * | 5/1984 | Kaule et al. | 428/199 |
| 4,650,320 A | * | 3/1987 | Chapman et al. | 356/71 |
| 4,893,558 A | * | 1/1990 | Gouch | 101/211 |
| 5,172,005 A | * | 12/1992 | Cochran et al. | 250/559.08 |
| 5,815,174 A | * | 9/1998 | Stone | 347/19 |
| 6,024,018 A | | 2/2000 | Darel et al. | |
| 6,998,623 B2 | * | 2/2006 | Usami et al. | 250/461.1 |
| 7,017,492 B2 | * | 3/2006 | Seymour | 101/484 |
| 7,129,506 B2 | * | 10/2006 | Ross et al. | 250/556 |
| 7,321,423 B2 | * | 1/2008 | Guttman | 356/319 |
| 7,438,378 B2 | * | 10/2008 | Reichelsheimer et al. | 347/19 |
| 2006/0213384 A1 | * | 9/2006 | Reinhard et al. | 101/216 |
| 2006/0261157 A1 | * | 11/2006 | Ostrowski et al. | 235/383 |

FOREIGN PATENT DOCUMENTS

| | | |
|---|---|---|
| EP | 1 149 703 A | 10/2001 |
| GB | 2 282 565 A | 4/1995 |
| WO | WO 02/065107 A | 8/2002 |

* cited by examiner

*Primary Examiner*—David P Porta
*Assistant Examiner*—David S Baker
(74) *Attorney, Agent, or Firm*—Clifford W. Browning; Krieg DeVault LLP

(57) ABSTRACT

A luminescence sensing device, comprising a plurality of optical sensor subunits, each said subunit comprising UV-illumination means for illuminating a sample; digital camera means, comprising a camera head; mirror means for directing light emitted from said sample onto said camera head; and a digital signal processor unit (DSP), processing signals generated by said camera head.

14 Claims, 6 Drawing Sheets

SENSING DEVICE

Applicant claims foreign priority benefits under 35 U.S.C. §§119(a)-(d) or (f), or §365(b) of European Patent Application No. 03405068.2, filed Feb. 10, 2003.

The present invention concerns a luminiscence sensing device, and a check system for detection and inspection of fluorescent or phosphorescent ink prints in a sheet fed security paper printing machine.

Printing press systems are typically subject to many variations and defects caused by changes in ink rheology, ink-water balance, temperature, etc. These variations and defects cause continuous changes in the colors within the print during the printing process.

Color quality control systems for monitoring deviations in color during the startup and continuous running phases of printing are known in the art. For example, U.S. Pat. No. 6,024,018 discloses a color control system for maintaining the color of a printed page of a printing press constant, within the context of the human perceptual color space system, comprising an elongated fluorescent lamp illuminating homogenously a strip of the print, a CCD camera acquiring an actual image of the printed sheet and a processing unit for analyzing colors of the actual sheet, measuring deviations from reference values and acting on ink keys of the printing machine.

In the sorting of used banknotes and other security papers it is becoming more and more common to use invisible features, in particular fluorescent or phosphorescent features, to distinguish between the different denominations, or to detect counterfeits.

It is therefore desirable to control prints of invisible luminescent inks—that is to say fluorescent or phosphorescent inks, absorbing UV light and re-emitting visible light, applied with a printing machine, for both quality of print as well as intensity of the signal.

Therefore a purpose of the invention is to provide a luminescent ink check system, capable of detecting and inspecting in real time running printed sheets of security papers, up to and above the maximum speed of the printing machine.

Another purpose of the invention is to provide a check system having the same capabilities for prints made with visible inks emitting in the IR region of the light spectrum. Still a further purpose of the invention is to provide a check system for prints made with iridescent inks.

A particular purpose of the invention is to provide a luminiscence sensing device, capable of running and inspecting printed sheets in real time and to process the datas transferring the luminescent images of the sheets to a host PC.

Such a check system should be designed with the operator in mind, so as to enable him to quickly identify defective prints and to undertake corrective action in case of under or over inking.

These aims are achieved by means of a sensing device, comprising a plurality of optical sensor subunits, each said subunit comprising

- illumination means, in particular UV-illumination means, capable of inducing luminescence of a defined portion of a sample;
- digital camera means, comprising a camera head;
- mirror means collecting and directing light emitted from said portion of said sample onto said camera head; and
- a digital signal processor (DSP) unit, processing signals generated by said camera head.

By means of a luminiscence sensing device according to the invention, in the running mode, an array of UV illumination sources excites the fluorescent or phosphorescent particles of printed invisible inks, inducing luminescence. An associated array of cameras and digital signal processor units detect and process this luminescent emission and send datas to a host PC. The software on this computer enables the data acquired and processed by the separate subunits to be merged together, displaying a single image of the inspected sheet on a control screen.

Preferably, the subunits are lined up in a row, whose length is sufficient to sense and inspect sheets having the maximal width feedable to the printing machine. Preferably the array of subunits is lodged within a common sealed housing. Since the housing is sealed, the delicate interior of the sensing device is protected from dust, lubricants and all solvents that are generally present inside a printing machine. The housing may be equiped with UV transparent windows, at least in the path of the UV beams emitted by the UV illuminating means.

Suitable digital camera means include CMOS cameras. The signal issued by each subunit-camera is processed by a digital signal processor unit. The DSP unit is connected to an interface, said interface comprising a fire wire bus, connecting all the DSP units to an external computer.

Luminescence emitted by a sample may have a low intensitiy, and thus, the mirror means of each optical sensor subunit preferably comprises a parabolic mirror for collecting light emitted by the inspected sample. This light is focused and sent to a counter-mirror, that in turn reflects said light and sends it through an objective of the camera head onto the photosensor of the camera.

The present invention offers an improvement for sheet fed security paper printing machines, namely the improvement consisting in a check system for detection and inspection of ink prints, in particular luminescent ink prints, said check system comprising a luminiscence sensing device, as described above, associated to computer means connected to said device by an interface, thereby comparing an acquired image of each of the printed sheets to programmed set values, in particular a set image of one or more said sheets.

Additionally, the check system may comprise an incremental encoder for identifying sheets and localising eventual misprints, and a sheet presence detector for triggering the checking and inspecting operations.

For sensing and inspecting sheets bearing fluorescent and phosphorescent inks having a weak luminiscence, the check system may comprise an additional UV illumination means. This extra illumination unit may consist of an array of UV tubes directed to the zone underneath the sensor subunits.

Preferably, the sensor housing, containing the sensor subunits lined up in a row, is arranged so that said row is parallel to the printed sheets and oriented crosswise to the direction of displacement of said sheets.

The accuracy of the measurement and quality of image of a sheet may be further enhanced by arranging a suction plate parallely to the row of sensor subunits, beneath the printed sheet, thereby rendering the measurement distance constant.

The sensor housing and the suction plate, facing one another, may be arranged in any position located downstream of the application of the luminescent ink, for example within a delivery section of the printing machine, in particular just upstream of a first delivery pile. This will allow the deviation of sheets containing defective print to be sent to a separate inspection pile, using the interface between the check system and the machine.

Further features and advantages of the present invention will appear to those skilled in the art by means of the description of a preferred embodiment in connection to the accompanying drawings, in which.

Figure 1:
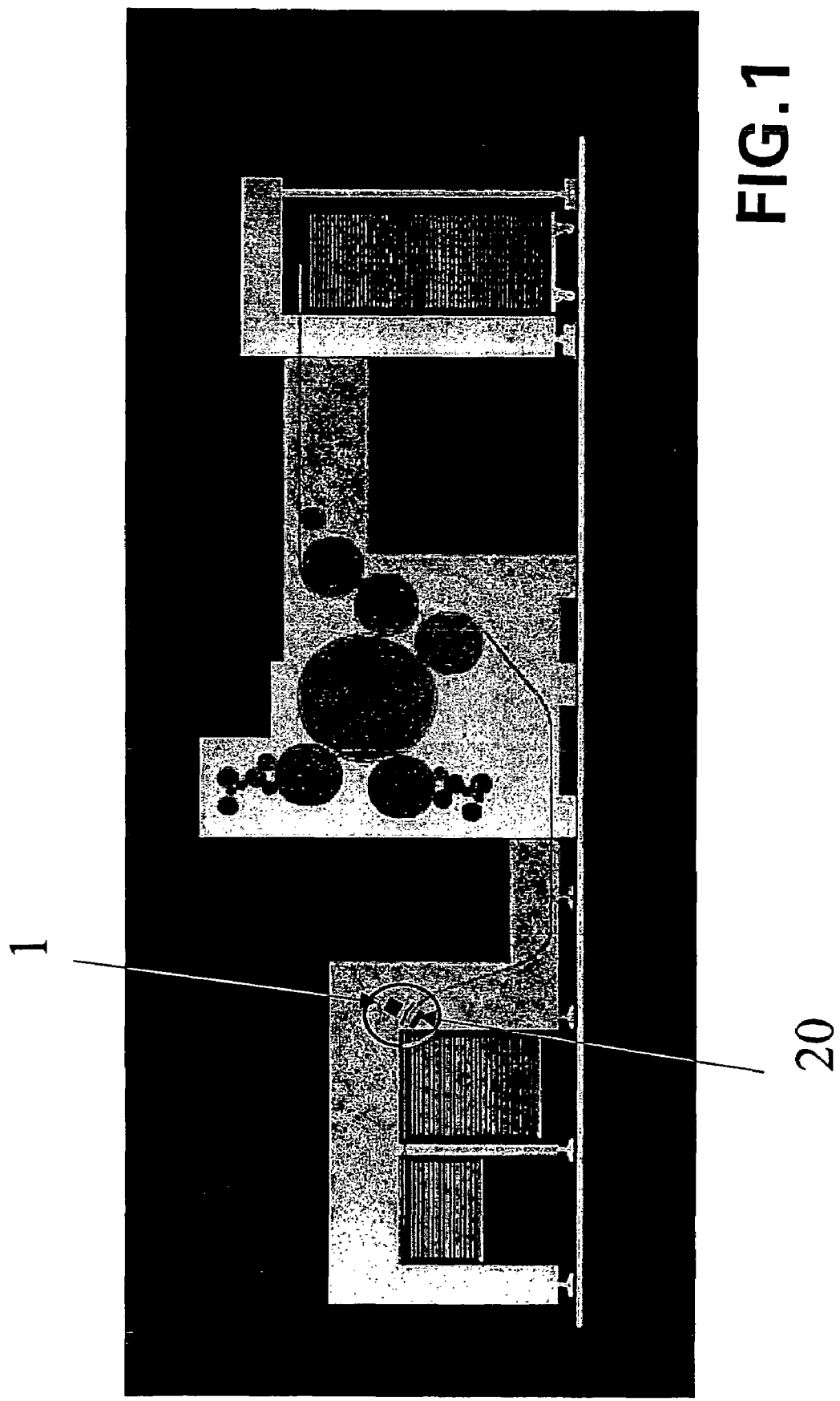
FIG. 1 is a schematic side view of a printing machine equipped with a check system according to the invention, showing a possible position of the sensor housing and of the suction plate.

FIG. 1 shows that in an existing sheet fed printing machine, a check system according to the invention may be provided as an improvement, downstream of the printing section itself, within the delivery section of the printed sheets, just upstream the first delivery pile. FIG. 1 shows schematically the position of the sensor housing 1 above the track of the printed sheets and the position of the suction plate 20, facing the sensor housing 1, and located just beneath the track of the sheets, thereby providing a constant distance between the surface of the inspected sheet and the luminescence sensing device.

Figure 2:
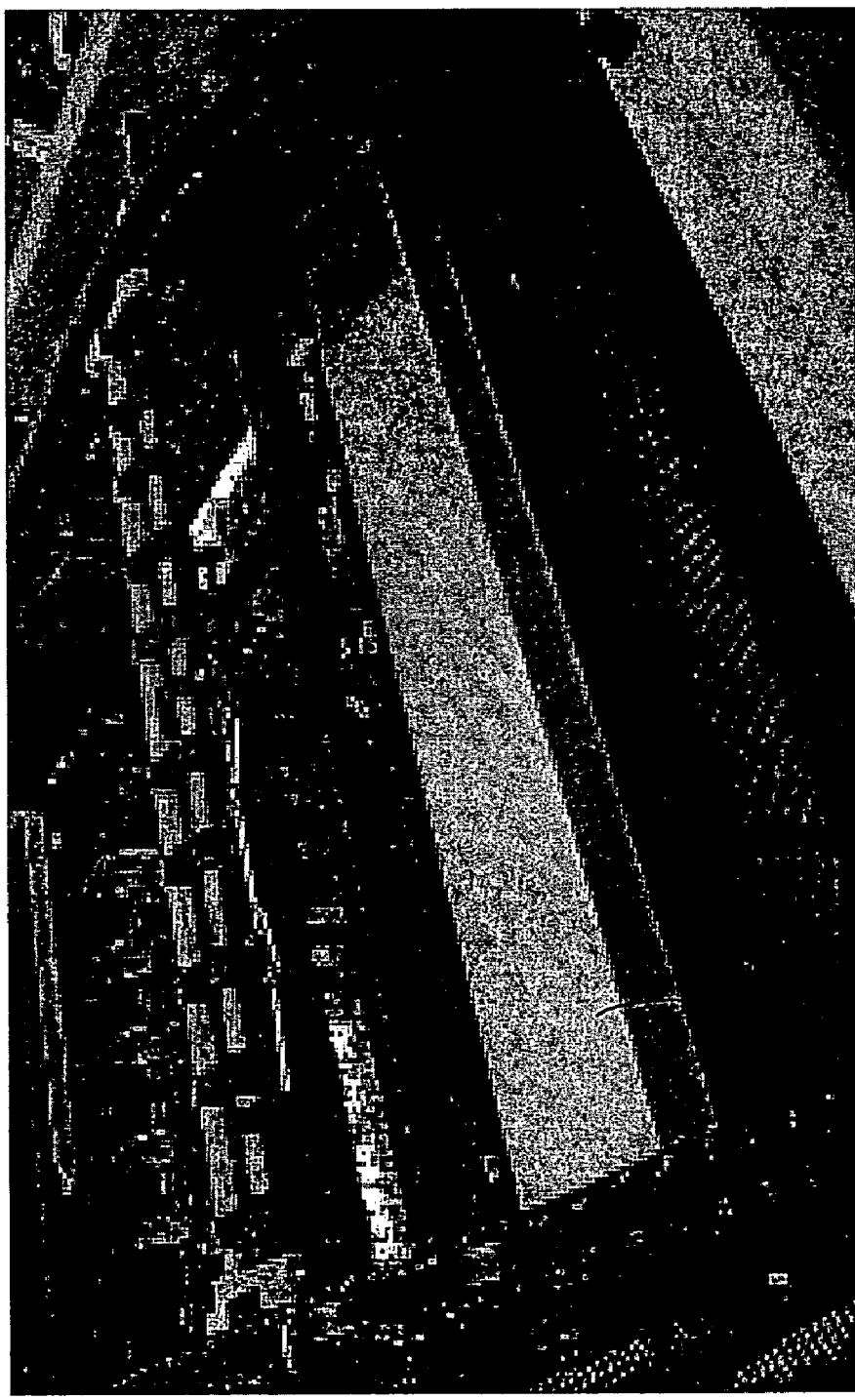
FIG. 2 is a photograph of a sensor housing and of a suction plate mounted on a printing machine.

FIG. 2 is a photograph illustrating the arrangement of the sensor housing and of the suction plate within a commercially available printing machine, a sheet-fed rotary letter press numbering machine of the type SuperNumerota 212™ of the manufacturer KBA-GIORI. As it may be seen from FIG. 2, the length of the luminescence sensing device is adjusted so as to cover the full width of the sheet track. The full length of the sensor housing is slightly greater than 800 mm. The number of optical sensor subunits, in this case five subunits, is selected so as to cover a total inspection length of about 800 mm with a slight overlapping of the fields inspected by the respective subunits, the field covered per camera/DSP subunit being slightly greater than 160 mm in width.

The suction plate shown by FIG. 2 consists of a perforated sheet metal plate, an array fans sucking the passing sheet down to the plate, ensuring a constant sheet-to-sensor distance.

Figure 3:
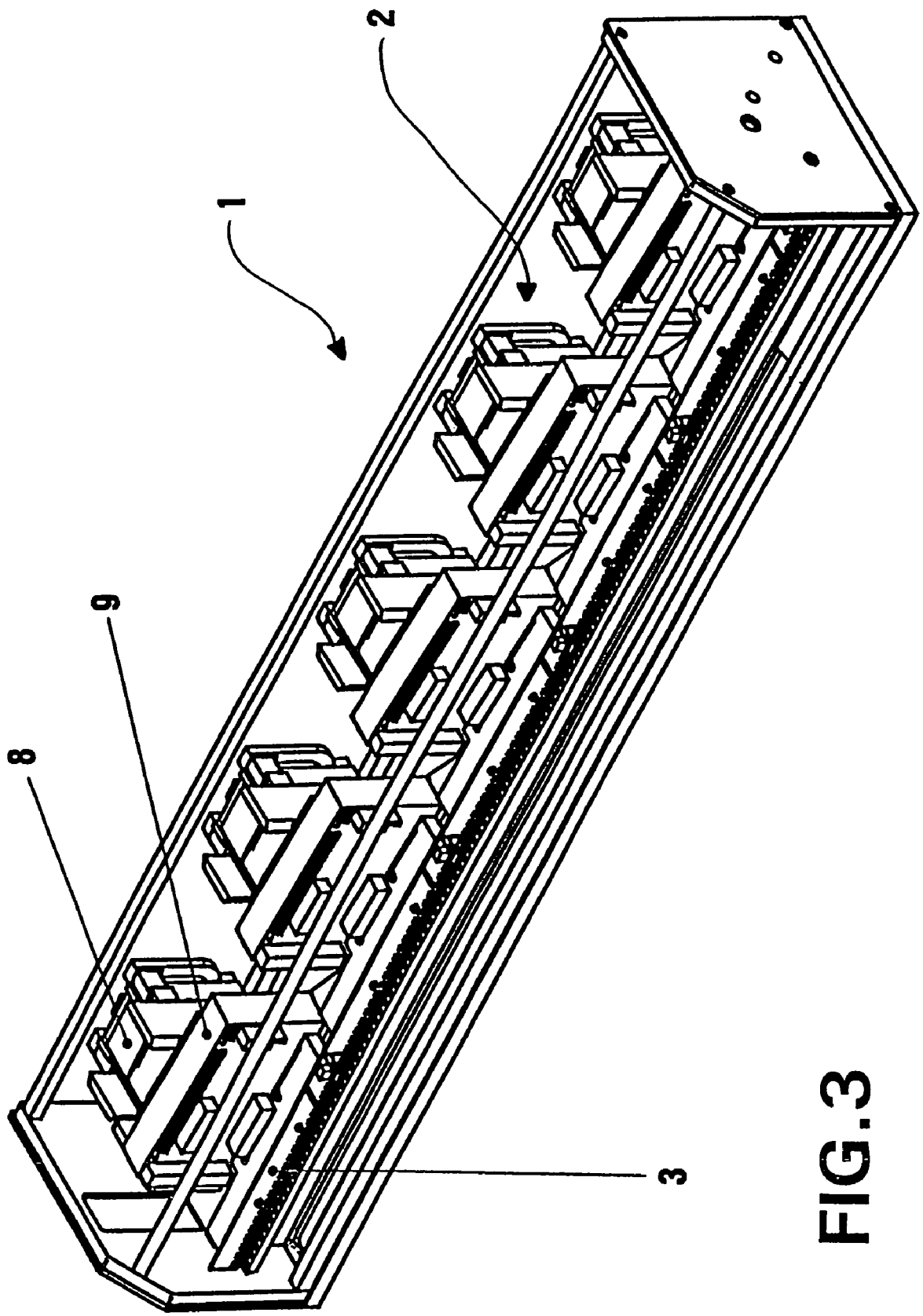
FIG. 3 is a drawing in perspective of the luminescence sensing device according to the invention, the upper cover of the housing being removed.

FIG. 3 shows a perspective view of the sensor housing 1, the upper cover being removed for the sake of clarity. Each sensor subunit 2 comprises an illumination means 3. The illumination means are selected among suitable monochromatic or broad-band light sources, like UV-LEDs, emitting for example a light at 375 nm, white light LEDs, IR LEDs, Mercury UV lamps, Deuterium UV lamps, etc, taking into consideration the absorption/excitation bands of the inks to be checked. The light beam of each illumination means is focused onto the sheet, so as to cover the sheet area alloted to the corresponding subunit. Thereby, intensity and control of the measured signals are enhanced, compared to the use of a single elongated tube illuminating the whole sheet width.

Figure 4:
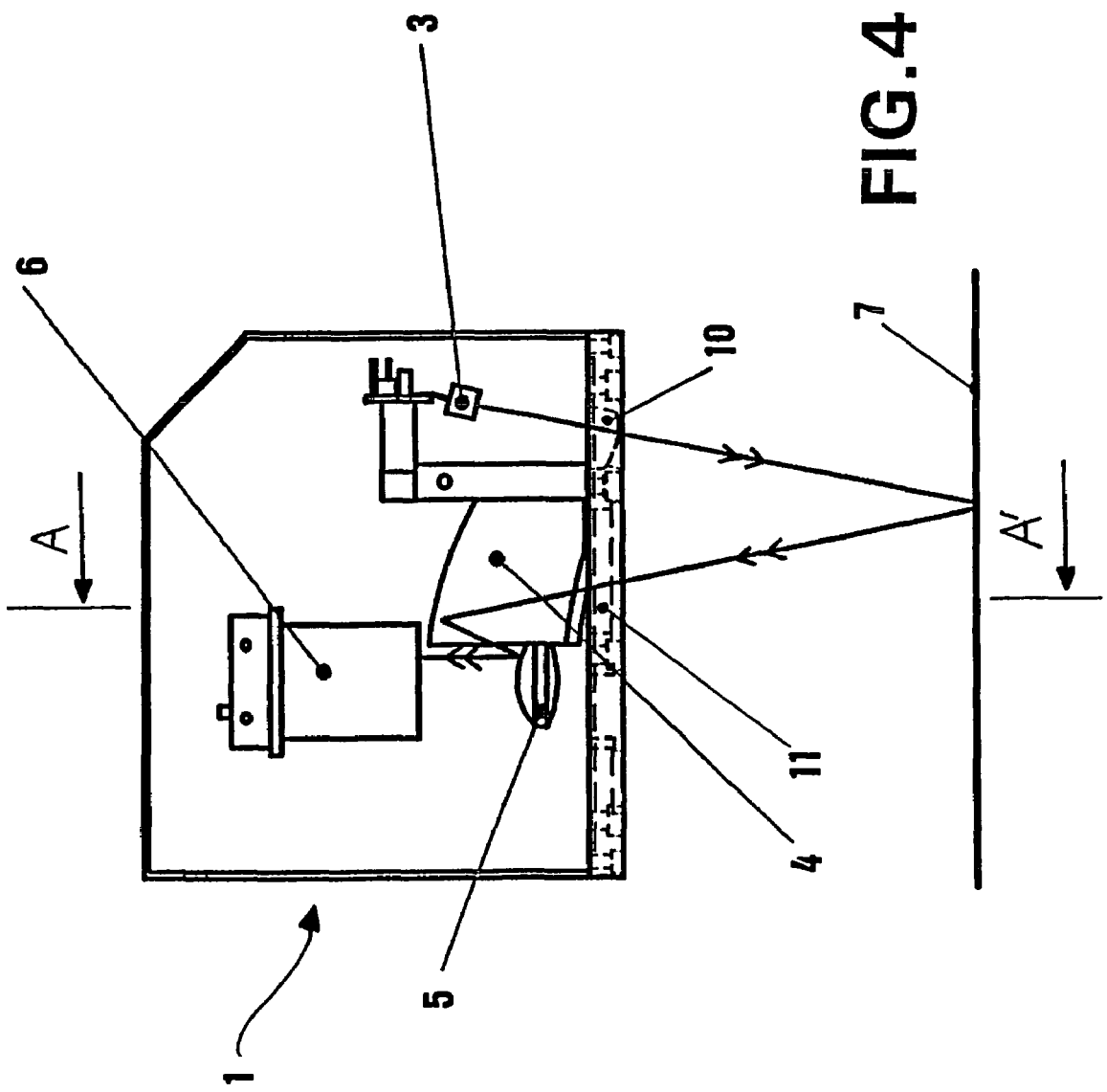
FIG. 4 is a schematic side view of a subunit illustrating the function of its components.
Figure 5:
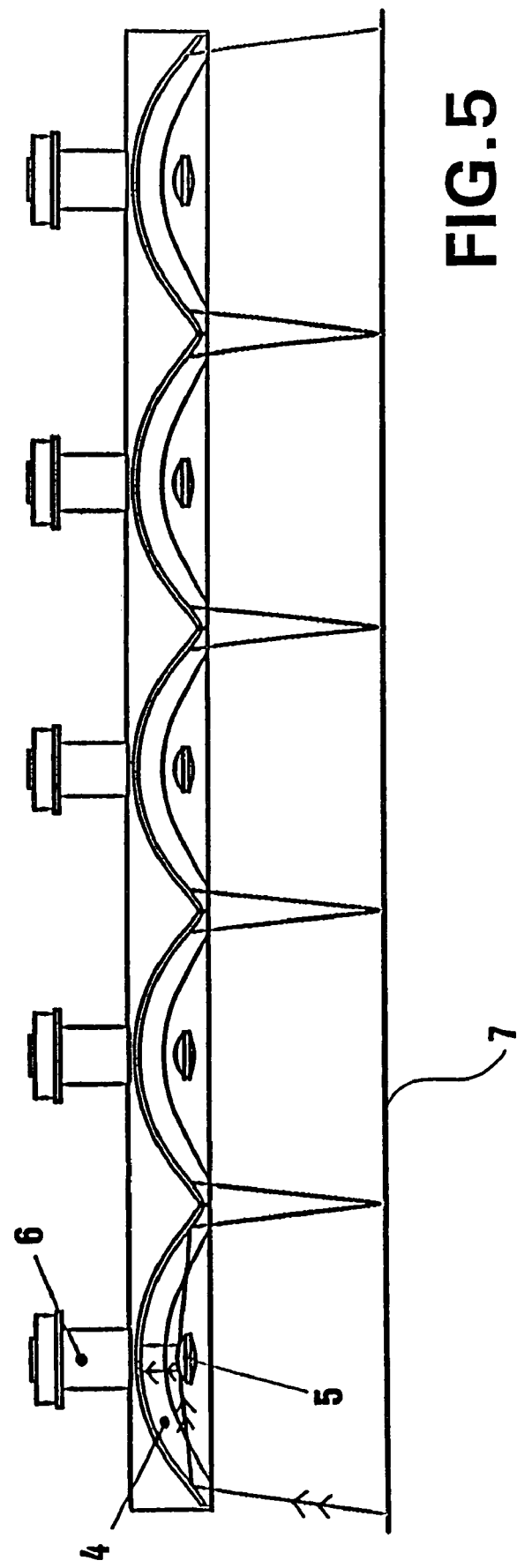
FIG. 5 is a schematic transverse section view of the luminescence sensing device along line AA' of FIG. 4.

As shown in FIG. 4 and FIG. 5, each subunit 2 comprises further a parabolic mirror 4 and a counter mirror 5 facing a camera head 6. FIG. 4 illustrates schematically the light path from the LED 3 to the running sheet 7 re-emitting fluorescent or phosphorescent light onto the parabolic mirror 4, which focuses the received light onto the counter mirror 5, which in turn reflects said light into the camera head. Light is received onto the optical sensor of each camera through a 6-mm objective.

The light emitted by the LED 3 crosses a first UV transparent window 10 to reach the sheet, and the re-emitted light penetrates back into the housing through a second window 11. If the second window 11 is not UV—transparent, only visible light, comprising the light re-emitted by fluorescence/phosphorescence will cross it, the reflected UV light being absorbed.

As shown by FIG. 3, each subunit 2 comprises a complete CMOS camera unit 8 and a DSP unit 9. CMOS cameras and DSP units are commercially available. It is possible to read out any specific line of the array from a CMOS camera, whereas this is not possible with a basic CCD camera. This ability enables an easy alignment of the plurality of cameras one to the other without complex mechanic procedures: the alignment is done by selecting the corresponding line of each camera so that the image from one camera lines up with the image of the next camera, providing a line scan camera. Therefore, CMOS cameras are preferred.

FIG. 5 shows that the array of five subunits permits to sense the full width of a sheet 7. Each parabolic mirror is about 160 mm wide. The row of five autonomous cameras and DSP units is connected to a host PC through a FIREWIRE (IEEE-1394 standard interface) bus for data connection and also to a separate power supply and to the sheet start and line impulse devices. FIREWIRE is a proprietary trademark of Apple, Inc.

The above-described arrangement of the five units allows a complete and continuous inspection line over a total width of slightly more than 800 mm. The sensing device is optimised for an inspection distance from the sheet surface of 100 mm. However the device can be easily adapted to other distances. The arrangement of the separate illumination means associated to each subunit, within the sensor housing, allows a very compact construction.

The check system comprises further an incremental encoder (not shown in the drawings), mounted on a transport cylinder, which rotates once per sheet. The presence of a sheet is controlled by a photoelectric proximity switch. A separate controller unit mounted in an operator's control desk guarantees a constant vertical resolution, for example 0.5 mm, on the basis of the output of these two components. A controller unit provides a start signal for each sheet and an impulse for every line of the passing sheet to the luminescence sensing device. The impulses are only generated if a sheet is present.

A control desk (not shown) serves as an interface to the sensing device for the operator. It is equipped with a PC, a flat screen, keyboard and mouse, allowing the set-up and handling of the sensing device. Additionally, signal lamps may be mounted on the desk, indicating the actual state of the device, for example a blue light, showing whether the inspection is active or not, a green, orange and red lamp serving as a visual alarm, and reporting deviations from the acceptable limits during the printing process. The control desk may further bear various commands and buttons allowing to cut the power from the sensing device, the illumination and the encoder controller unit. The control desk also houses an uninterruptible power supply, which buffers potential power cut-offs. The PC, housed also in the control desk, may be equipped with a CD writer to backup check set-up data. Further power supplies and relays are provided in the control desk for powering the warning lamps on the desk and the above-mentioned controller units.

The user interface of the check system is provided with the following functions:

a. Sensing Device Set-up:

The sensing device set-up has only to be done once, before the very first operation, and remains the same for the lifetime of a particular sensing device.

b. Inspection Set-up:

To start the definition of a new inspection set-up, a reference sheet or sheets is (are) acquired and recorded and the various regions of interest (ROI) and their parameters are set. During the sheet set-up, the total width and height of the printed sheet are defined by setting the borders around the printed area. The general layout of the bank notes or other security papers is also defined and distributed on the sheet according to the entered number of columns and rows. A fine adjustment of the layout can be done manually. The regions of interest (ROI) can be defined for a single bank-note/security paper and are then copied automatically to all other according columns and rows.

Different possibilities to control regions of interest are implemented in the check system software. A first one is adapted for the evaluation of cliche type ROIs 22. It computes the average intensity of the defined ROI area and compares this average with thresholds defined by the operator.

A second algorithm detects barcodes within a defined ROI 23 and compares them with a master template.

c. Inspection, Running Mode:

During production, the check system software displays the actual states of the different ROIs in a clear manner and constantly informs the printer about possible problems of the printing process. The software also plots tendencies of under or over inking allowing the printer to undertake corrective action even before defective print is produced. Inspection results are displayed in real time with alarm warning and good inspection identification.

Figure 6:
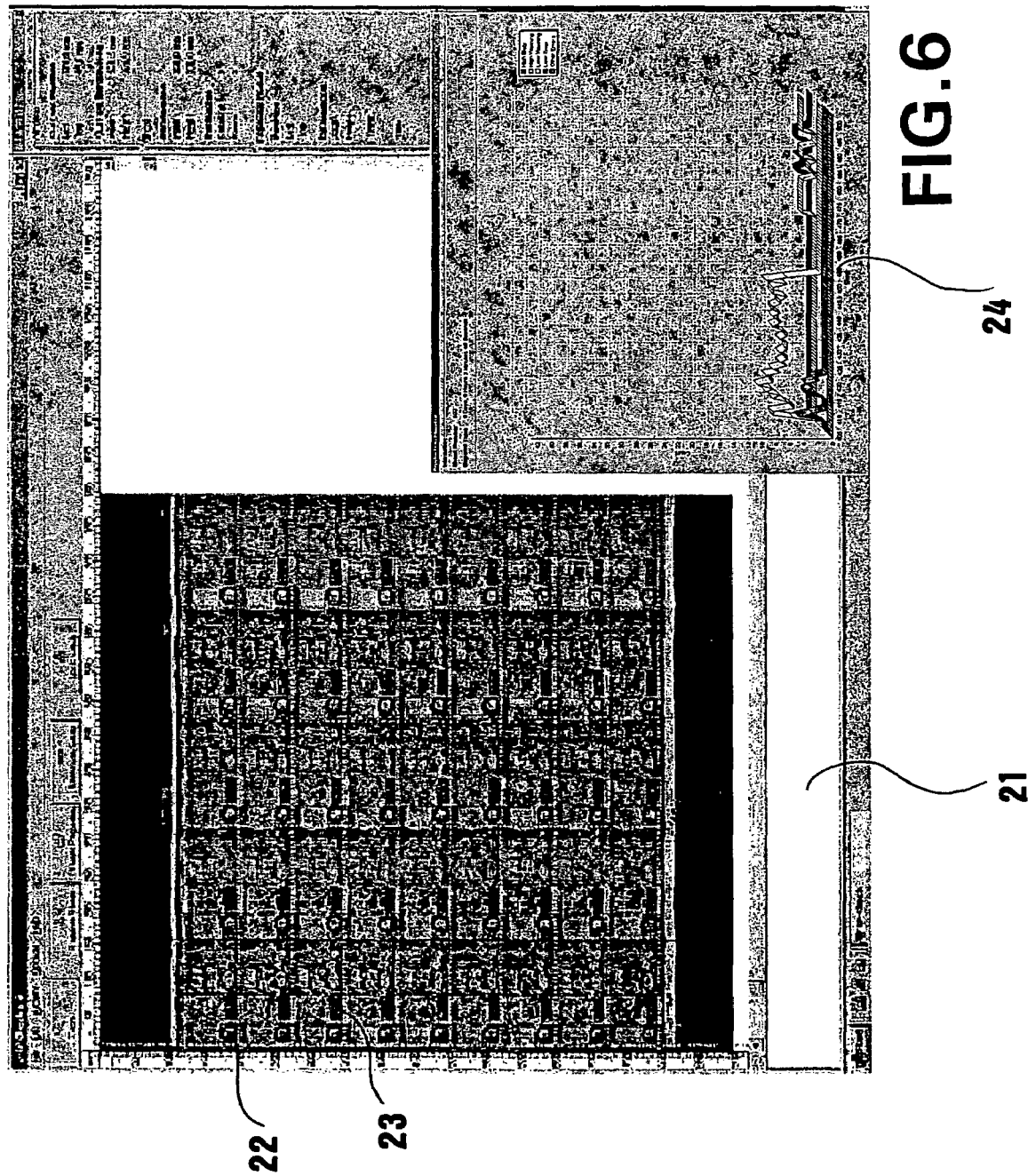
FIG. 6 shows an example of a production window and production monitor window of the control desk.

During the production—if the inspection is active—the sensor's output is visualised in real time on the screen of the control desk in two different manners (see FIG. 6):

The main window 21 gives an overview of the sheet. The momentary ROIs' states 22 and 23 are visualised with coloured frames, which are updated after every sheet. The frames are green as long as everything is correct and the average values of the ROIs are within the set thresholds or the barcodes are recognised correctly.

As soon as a ROI's average exceeds one of the thresholds, the color of its frame gradually changes to either blue or red. A tendency to blue signifies that there is over inking and the ROI's average is too high. On the other hand a tendency to red shows that there is under inking and the ROI's average is rather too low. Changing colors are accompanied by a message indicating how many graylevels the measured average differs from the defined threshold. Messages "−1" to "−9" or "+1" to "+9" or the like are warnings and are accompanied by the lighting yellow warning lamp. The messages "too low" or "too high" stand for errors where the thresholds are exceed by more than e.g. 10 graylevels. Errors are accompanied by lighting yellow and red lamps on the control desk.

In addition to the main window, the production monitor window 24 shows tendencies of the printing process. It displays the results of the last sheets. Five parameters are shown: the number of general errors, the number of "low" warnings, the number of "low" errors, the number of "high" warnings, the number of "high" errors per sheet, and the number of barcode errors. Barcode errors occur whenever the check system detects no or a wrong barcode.

Those skilled in the art will understand that within the framework of the invention, the illumination means may also be selected among visible or IR-illumination sources, depending upon the absorption wavelegths of the ink, and that the appropriate corresponding camera-photosensors may detect light re-emitted by prints, e.g. images, printed by means of iridescent inks or visible inks having different emitting IR wavelengths.

The invention claimed is:

1. A luminescence sensing device, comprising a plurality of optical sensor subunits, lined up in a row within a common sealed housing, each said subunit comprising within said housing
    illumination means capable of inducing luminescence of a defined portion of a sample;
    digital camera means, comprising a camera head;
    mirror means collecting light emitted from said portion of said sample and directing it onto said camera head, said mirror means consisting of a parabolic mirror and counter mirror; and
    a digital signal processor (DSP) unit, processing signals generated by said camera head.

2. A device as claimed in claim 1, wherein said camera means is a CMOS camera.

3. A device as claimed in claim 1, further comprising an interface, said interface comprising a FIREWIRE (IEEE-1394 standard interface) bus, connecting said DSP units to a computer.

4. A device as claimed in claim 1, wherein said illumination means are UV illumination means and wherein said housing comprises a UV transparent window.

5. A check system for detection and inspection of fluorescent or phosphorescent ink prints in a sheet fed security paper printing machine, said check system comprising a device as claimed in claim 1, and computer means connected to said device, comparing an acquired image of each of said sheets to a set image of a said sheet.

6. A check system as claimed in 5, wherein said computer means are connected to said device by an interface comprising a FIREWIRE (IEEE-1394 standard interface) bus, connecting said DSP units to said computer means.

7. A check system as claimed in claim 5, wherein said row is arranged parallely to said sheets and crosswise to the displacement of said sheets.

8. A check system as claimed in claim 7, further comprising a suction plate arranged parallely to said row.

9. A check system as claimed in claim 5, further comprising an additional illumination means outside said housing.

10. A check system as claimed in claim 5, arranged at a delivery section of said printing machine upstream a first delivery pile.

11. A check system as claimed in claim 5, wherein said camera means is a CMOS camera.

12. A check system as claimed in claim 5, wherein said illumination means are UV illumination means and wherein said housing comprises a UV transparent window.

13. A check system for detection and inspection of fluorescent or phosphorescent ink prints in a sheet fed security paper printing machine, said check system comprising a luminescence sensing device, comprising a plurality of optical sensor subunits, lined up in a row within a common sealed housing, each said subunit comprising within said housing:
    illumination means capable of inducing luminescence of a defined portion of a sample;
    digital camera means, comprising a camera head;
    mirror means collecting light emitted from said portion of said sample and directing it onto said camera head; and
    a digital signal processor (DSP) unit, processing signals generated by said camera head, wherein said check system further comprises computer means connected to said luminescence sensing device, comparing an acquired image of each of said sheets to a set image of said sheet, wherein said row is arranged parallely to said sheets and crosswise to the displacement of said sheets, and wherein a suction plate is arranged parallely to said row.

14. A check system for detection and inspection of fluorescent or phosphorescent ink prints in a sheet fed security paper printing machine, said check system comprising a luminescence sensing device, comprising a plurality of optical sensor subunits, lined up in a row within a common sealed housing, each said subunit comprising within said housing:

illumination means capable of inducing luminescence of a defined portion of a sample;

digital camera means, comprising a camera head;

mirror means collecting light emitted from said portion of said sample and directing it onto said camera head; and a digital signal processor (DSP) unit, processing signals generated by said camera head, wherein said check system further comprises computer means connected to said luminescence sensing device, comparing an acquired image of each of said sheets to a set image of said sheet, wherein said check system is arranged at a delivery section of said printing machine upstream a first delivery pile.

* * * * *